United States Patent [19]

Green et al.

[11] Patent Number: 4,554,248

[45] Date of Patent: Nov. 19, 1985

[54] COMPOSITION AND METHOD FOR DETECTING ANTISTREPTOLYSIN O

[75] Inventors: Lorrence H. Green, Westbury; John W. Roberts, Commack, both of N.Y.

[73] Assignee: American Home Products Corporation, New York, N.Y.

[21] Appl. No.: 440,049

[22] Filed: Nov. 8, 1982

[51] Int. Cl.$^4$ .................... G01N 33/54; C12Q 3/00; C12Q 1/00; C12Q 1/04; C12Q 1/06; C12N 9/99; C12N 1/36; A61K 39/02

[52] U.S. Cl. ........................................ 435/7; 435/34; 435/4; 435/6; 435/39; 435/243; 435/3; 435/184; 435/68; 435/245; 435/885; 436/522; 424/88; 424/92

[58] Field of Search ................. 436/522; 435/4, 6, 7, 435/3, 34, 36, 39, 243, 184, 68, 885, 245; 424/92, 88

[56] References Cited

U.S. PATENT DOCUMENTS

| | | | |
|---|---|---|---|
| 4,148,609 | 4/1979 | Ricci | 435/13 |
| 4,172,126 | 10/1979 | Okonagi et al. | 435/885 |
| 4,376,819 | 3/1983 | Brown et al. | 435/7 |
| 4,379,850 | 4/1983 | Ricci | 456/522 |
| 4,508,831 | 4/1985 | Toth | 436/512 |

OTHER PUBLICATIONS

Morrison & Boyd, *Organic Chemistry,* 1977, p. 33, Allyn & Bacon Inc.

Dassy, B. et al., *Journal of Gen. Microbiol.,* vol. 129, pp. 643–651, (1983), "Growth of *Streptococcus pyogenes* and Streptolysin O Production in Complex and Synthetic Media.

G. C. Klein et al., Appl. Microbiol., 21, No. 6, 999–1001, (1971).

A. Ricci et al., J. Clin. Microbiol., 8, No. 3, 263–267, (1978).

L. A. Rantz et al., Proc. Sec. Exp. Biol. Med., (N.Y.), 59, 22–25, (1945).

G. C. Klein, Man'l Clin. Imm., 2nd Ed., Ch. 57, 431–440, (1980).

*Primary Examiner*—Thomas G. Wiseman
*Assistant Examiner*—Robin Teskin
*Attorney, Agent, or Firm*—Adley F. Mandel

[57] ABSTRACT

A composition is used as a reagent in a method for measuring Antistreptolysin O (ASO) in a blood sample. The composition contains Streptolysin O (SO) at a pH outside the range of its hemolytic activity, e.g., outside the pH range of 5–9. At that pH the SO is reversibly inactivated while maintaining its hemolytic capacity. The composition is employed to measure ASO by mixing one or more samples of non-hemolyzed blood or serum with one or more known quantities of the composition with a known hemolytic capacity, incubating each mixture to allow reaction of any ASO in the sample with the SO, restoring the hemolytic activity of the SO by adjustment of pH to permit lysis and detecting the presence or absence of lysis in each sample.

17 Claims, No Drawings

COMPOSITION AND METHOD FOR DETECTING ANTISTREPTOLYSIN O

BACKGROUND OF THE INVENTION

Streptolysin O (SO) is a hemolytic protein produced by most group A streptococci. One property of SO is its antigenicity with the result that antistreptolysin O (ASO) is usually produced in response to Streptococcus A infections. While ASO binds SO and inhibits SO hemolytic activity, the amount of ASO produced in response to the infection may be in excess of the amount required to inhibit the SO. Moreover, repeat infections frequently trigger an amplified immune response and excess production of ASO. Because ASO also bonds to M type proteins, this leads to secondary immune responses, the sequellae of which include degeneration or destruction of certain heat and kidney tissues which may result in rheumatic fever or acute glomorulonephritis.

It is also well known that SO hemolytic activity is neutralized or destroyed in its oxidized state. Since the SO antigen is readily available commercially and because of the described properties of SO and ASO, the measurement and monitoring of a patient ASO titer has been a feasible and useful diagnostic tool.

Most commercially available kits for determining ASO titer are based on the Rantz and Randall methodology Proc. Sec. Exp. Biol. Med. (N.Y.) 59,22 (1945). The procedure calls for the technician to draw several mls of blood, and then process it into serum. The serum is then diluted and incubated at 37° C. with SO. After an initial incubation period of 15 minutes, a constant amount of 5% washed rabbit, sheep, or human type O red blood cells (RBC's) are added, and the samples are again incubated. ASO titer is determined about 45 minutes later by noting which tubes contain lysed RBC's. The procedure is very time consuming and tedious. It also has several steps at which pipetting errors can easily occur and cause inaccurate results. In addition, it requires that the technician have access to a centrifuge, an incubator, and a fresh supply of washed 5% RBC's.

A more recent procedure is described by Ricci et al., j'l Clin. Microb., Vol. 8, no. 3, 263-267 (1978) and in U.S. Pat. No. 4,148,609 issued Apr. 10, 1979. In the Ricci method SO is chemically altered through oxidation to form disulfide bonds, chemically inactivating the hemolytic activities of the molecules. After incubating the oxidized SO with a blood sample possibly containing ASO, the SO is once again chemically altered with a reducing substance to reactivate the SO hemolytic activity. The SO in excess of that necessary to bind all the available ASO is then free to lyse the erythrocytes in the blood sample.

In most of these tests for determining ASO, the measurements are expressed in Todd Units. Thus one Todd Unit (TU) of SO has been arbitrarily defined as the amount of SO needed to completely lyse 1 ml of 5% red blood cells in saline in one hour at 37° C. Correlatively one TU of ASO has been defined as that amount of ASO which bonds to 2½ TU of SO. Whether one uses Todd Units or any other unit, arbitrary or otherwise, correlating the hemolytic activity of SO with its ability to bind with ASO, however, is a matter of choice, so long as such expressions or measurements are related to the observed ASO values of normal and diseased patients.

In this disclosure the term "hemolytic activity" has been used and is defined as the ability of SO to lyse blood cells; and the term "hemolytic capacity" has been used and is defined in relation to the amount of hemolytic activity and correlatively the amount of binding ability to ASO possessed by SO.

SUMMARY OF THE INVENTION

This invention provides compositions of Streptolysin O (SO) which are useful as reagents in measuring or determining, either qualitatively or quantitively, the antistreptolysin O (ASO) titer of an unknown sample of blood, usually human blood. The composition of this invention comprises a solution of SO having a pH essentially outside the pH range wherein SO possesses hemolytic activity. Advantageously the composition of the invention is employed in a dry form which can be achieved by lyophilizing, vacuum drying or other methods known in the art.

The advantages of the present invention stem from the discovery that the hemolytic activity of SO is sensitive to pH. Thus it has been found that the hemolytic activity of SO can be reversibly neutralized or inactivated by adjusting the pH of the composition outside the hemolytic activity range of SO without substantially affecting or reducing the hemolytic capacity of the SO so treated. As a result when the pH of an SO containing composition is readjusted to within the hemolytic activity range of SO, the hemolytic capacity of the SO in the composition is restored or reactivated. Accordingly, in another embodiment, this invention includes a method for reversibly inactivating the hemolytic capacity of SO comprising the step of adjusting the pH of an SO composition or solution to a pH outside the pH range wherein SO possesses hemolytic activity.

Still another embodiment of this invention relates to a method for measuring the ASO titer or concentration in a sample of blood whether whole blood or the serum thereof. Broadly stated, this method involves, first, mixing at least one sample of non-hemolyzed blood with at least one predetermined quantity of SO. The mixing is achieved in a non-hemolytic solution, the pH of which is outside the hemolytic activity range of SO and the SO employed in the method has a known hemolytic capacity.

In a second step each solution is incubated for a time sufficient to allow any ASO in the blood sample to react (or bind) with the SO. The hemolytic activity of the unbound SO is then restored (or reactivated) by adjusting the pH of each incubated solution to a range within the hemolytic activity range of SO, whereby any free (or unbound) SO in excess of the amount required to react with the ASO can lyse blood, i.e., the blood cells. The final step of the method involves detecting the presence or absence of lysis in each solution.

DETAILED DESCRIPTION OF THE INVENTION

In one aspect, this invention relates to a composition comprising Streptolysin O (SO) at a pH outside the hemolytic activity range of SO or outside a pH of from about 4.8 to about 9.0 and preferably from about 4.6 to about 9.5–9.6. The usefulness of the composition of the invention, whether in solution or dried form, arises from the discovery that the hemolytic activity of SO is reversibly sensitive to pH. Accordingly the composition can be employed as a reagent for the detection or measurement of antistreptolysin O (ASO) or for monitoring the course of a disease state or infection or the effectiveness of a course of treatment against a disease state or infection which produces ASO antibody in response to a group A streptococcus infection.

While not wishing to be bound by any theory of invention, it is believed that hemolytic activity is optimized at certain pH ranges and as the pH is adjusted outside such an optimum range, the hemolytic activity undergoes a progressive pH induced change in the conformation of the (hemolytically) active site of SO. Also, while the adjustment of the pH to a pH outside the hemolytic activity range of SO can totally inhibit SO hemolytic activity, such adjustment does not affect SO binding or reaction sites to ASO or otherwise destroy or permanently inactivate the hemolytic capacity of the SO so treated.

Another advantage of the composition and method of the invention is that the use of the invention does not require separation of the serum from blood or stripping the blood serum from its complements. While the method of the invention allows the use of such separated fractions, the method may be most advantageously conducted on whole blood using even small samples thereof.

The composition of the invention employs an otherwise hemolytically active form of SO, the activity of which has been reversibly inactivated by the previously described pH adjustment to a pH outside the hemolytic activity range of SO. More particularly the composition and method of the invention utilize the hemolytically active, reduced form of SO.

While there are many routes to obtaining the hemolytically active form of SO, the following procedure was advantageously employed. A hemolytic strain of *Streptococcus Pyrogenes* Type I (Group A), which had been stored frozen, was thawed, streaked on an agar plate containing 5% blood and incubated at 37° C. for 18–24 hours. Colonies from this first plate were streaked and incubated on a second plate under the same conditions. Several colonies from the second plate were then used to inoculate 10 ml of Todd-Hewitt (TH) broth which was then incubated at 37° C. for 18–24 hours. Following incubation 1.0 ml of the first TH suspension was inoculated into a second tube containing 10 ml of TH broth and incubated and then 1 ml from the second tube is inoculated into a third container having 100 ml of TH broth. The one hundred milliliters of the last incubated suspension was then inoculated into 10 liters of TH broth, incubated at 37° C. and then 25° C. until all the bacteria settled, after which the bacteria was removed by filtration. The filtrate containing SO may be stored frozen after adjusting the pH to about 6.75. Prior to use, the SO in the filtrate is reduced to restore and preserve SO hemolytic activity which may have been lost in the preparation of the SO through oxidation. Cysteine is the preferred reducing agent although other reducing agents known in the art for reducing SO may be used.

According to one embodiment of conducting the method of the invention one or more predetermined quantities of the hemolytically active form of SO may be mixed with at least one sample of non-hemolyzed blood in a non-hemolytic solution having a pH outside the hemolytic activity range of SO. Alternatively, the pH of the filtrate or solution containing the hemolytically active SO is adjusted to a pH outside the hemolytic activity range of SO to provide the composition of the invention preferrably to a pH of about 9.4 and most preferrably to a pH of about 9.5–9.6 or higher and with a basic substance such as sodium or potassium hydroxide and the like and/or buffer. While the pH adjusted (inactivated) SO may be stored frozen, it is preferrable to immediately employ said SO in an appropriate dilution or dilutions, by mixing with at least one sample of non-hemolyzed blood whereby the pH of the mixed solution remains outside the hemolytic activity range of SO in another embodiment of conducting the method of the invention. Most preferrably, the filtrate (solution) containing the hemolytically active (reduced) SO is vaccum dried either, in predetermined quantities or dilutions, directly in a test chamber or chambers, or, dried and then placed in the test chamber or chambers. The composition of the invention in dry form is stable at room temperature but storage under refrigerated conditions provides longer stability. As noted elsewhere, the hemolytically active SO employed in the invention will have a known or predetermined hemolytic capacity.

Thus, the invention provides a method for measuring the antistreptolysin O (ASO) titer in a sample of blood comprising the steps of (a) mixing at least one sample of non-hemolyzed blood with at least one predetermined quantity of Streptolysin O (SO) in a non-hemolytic solution having a pH outside the hemolytic activity range of SO, said SO having a known hemolytic capacity;

(b) incubating each solution at a temperature of about 0°–50° C. for a time sufficient to allow any ASO in the blood sample to react with the SO;

(c) restoring the hemolytic activity of the SO by adjusting the pH of each incubated solution to range within a pH of about 4.8 to about 9.0, whereby any free SO in excess of the amount required to react with the ASO can lyse blood; and (d) detecting the presence or absence of lysis in each solution.

The method of this invention for measuring ASO titer is quite flexible and lends itself to various advantageous pathways. For example, the composition of the invention may be employed either directly in solution or dry form, or indirectly through the introduction and mixing of SO into a non-hemolytic solution at a pH outside the hemolytic activity range of SO with or without the blood sample. Similarly the SO in solution or dry form, may be added to the blood sample or the blood sample may be added to the SO. The method is further adaptable to using equal or graduated volume(s) or amount(s) of the blood sample and to using equal or graduated concentrations of the SO in liquid or dry form. The method of the invention as described is also adaptable to the inactivation or inhibition of the hemolytic activity on either side of the pH range outside of which SO possesses hemolytic activity. However, the invention is most advantageously conducted when the inactivation results from raising or maintaining the SO pH, i.e. to a pH greater than about 9, preferrably to a pH greater than about 9.4 and most preferrably to a pH greater than about 9.5–9.6. On the acid side the analogous progression to the most preferred pH is less than respectively about 5, 4.8 and 4.6.

After mixing a particular amount or dilution of the blood or serum sample with the SO, the solution formed is incubated for a time sufficient to allow any ASO in the sample to react or bind with the SO. In this invention a time of about 1 to about 10 minutes has proved sufficient, although longer incubation periods and a time as short as one minute are acceptable. The incubation temperature may range from about 0° C. to about 50° C., but is preferably from about room temperature (18°-21° C.) to 50° C. and most preferably about 20°-25° C.

Depending on which end of the pH range has been employed to inhibit or reversibly inactivate the SO hemolytic activity, either an acidic or basic substance, preferably a buffered substance will be used to restore the SO hemolytic activity by adjusting the pH of the incubated solution within the hemolytic activity range. The step of restoring hemolytic activity may also be advantageously applied employing a reducing substance such as cysteine together with the buffer substance or with a reducing buffer per se. In this way, prophylaxis towards oxidation would not be a concern nor would the use of an initially reduced form of SO be required. Other buffers which may be employed include sodium and/or potassium sulfite, phosphate, thiosulfate or thiosulfite; imidazole; citrate; 2-N-morpholino ethane sulfonate and the like.

Accordingly while the pH may be adjusted within the range of 4.8 to 9.0, full hemolytic capacity is best restored within the range of about 6 to 8, and most particularly within the range of about 6.5 to about 7.0. Once the activity is restored, excess SO not bound or reacted with the ASO present in the sample will proceed to lyse the blood cells also present in the sample.

While lysis of the cells will immediately begin once hemolytic activity is restored it is best to wait or incubate the solutions at least 1-2 to about 10 minutes before detecting the presence or absence of lysis in each solution. Generally, the recommended time to wait or incubate before detection will depend on whether a qualitative or quantitative test for ASO is desired. In the former case, typically, only one blood sample is being tested against one quantity of SO and accordingly less time is efficacious. In the latter case more than one test is studied at one time and accordingly the incubation time prior to detection should preferrably range over at least 5 to 10 minutes.

Conveniently, lysis can be detected immediately after incubation. To avoid false or misleading results, however, it is advisable to detect the presence or absence of lysis within about 20 minutes after incubation restoring SO hemolytic activity and preferrably within about 10 or about 15 minutes. In sum detection of the presence or absence of lysis will normally be made within about 1 to 30 minutes following the pH adjustment restoring SO hemolytic activity and the preferred times will range over the various sums of the waiting (incubation) and detection times indicated.

The presence of lysis will result in a clear solution and the absence of lysis or incomplete lysis will be indicated by the presence of turbidity in the solution. For practical purposes; positive and negative controls are desirable but not necessary.

As described, the method of this invention for measuring the ASO titer in a sample of blood is most conveniently and preferrably conducted with a small sample of whole blood which is readily obtained, for example, by ear, heel or finger puncture. Anticoagulants or anticoagulated blood are not required for the test when the blood sample is immediately diluted for use. For example 40 microliters of the blood may be diluted with 2.0 ml of physiological saline and a volume or equal volumes of the diluted blood are introduced into one or a series of test chambers. Aside from any controls, each test chamber contains graduated amounts of the composition of this invention. The sample is mixed with the SO in each test chamber and the solution thus formed is incubated. The pH of each incubated solution is then adjusted within the range of 6 to 8 and the presence or absence of lysis is detected.

What is claimed is:

1. A dry reagent composition suitable for measuring the amount of Antistreptolysin O in a sample which comprises a reversibly hemolytically inactive Streptolysin O in dry form and a member selected from the group consisting of an acid, base or buffer in an amount sufficient to maintain the pH of said composition greater than about 9.0 or less than about 4.8.

2. The composition of claim 1 having a pH of greater than about 9.5 to 9.6 and less than about 4.6.

3. The composition of claim 1 having a pH of greater than about 9.5 to 9.6.

4. The composition of claim 1 in solution.

5. The composition of claim 3 in solution.

6. A method for preparing a dry reversibly hemolytically inactive Streptolysin O (SO) reagent comprising mixing SO with a member selected from the group consisting of an acid, base or buffer in amount sufficient to maintain the pH greater than about 9 or less than about 5; drying the mixture, and isolating the dried reversibly hemolytically inactive SO which is suitable for analytical use for the detection of Antistreptolysin O(ASO) in a sample.

7. The method of claim 6 wherein the pH is adjusted to a pH at least greater than about 9.5 and less than about 4.8.

8. A method for measuring the Antistreptolysin O (ASO) titer in a sample of blood or serum comprising the steps of (a) mixing at least one sample of non-hemolyzed blood or serum with a predetermined quantity of Streptolysin O (SO) in a non-hemolytic solution having a pH outside the hemolytic activity range of SO, said SO having a known hemolytic capacity, and the pH of said solution being greater than about 9 or less than about 4.8;

(b) incubating each solution at a temperature of about 0°–50° C. for a time sufficient to allow any ASO in the sample to react with the SO;

(c) restoring the hemolytic activity of the SO by adjusting the pH of each incubated solution to a pH to greater than about 9.0 or less than about 4.8, whereby any free SO in excess of the amount required to react with the ASO will then proceed to lyse the blood cells present in the sample:

(d) determining the ASO titer by detecting the presence or absence of lysis in each solution whereby a clear solution indicates the presence of lysis and an ASO titer of the sample less than that needed to bind the known quantity of SO, and a turbid solution indicates the absence of lysis and an ASO titer in the sample equal or greater than that needed to bind the known quantity of SO.

9. The method of claim 8 in which step (a) further comprises (1) preparing at least one solution of SO having a pH outside the hemolytic activity range of SO; and (2) mixing a volume of each SO solution with a blood or serum sample, whereby the pH of the mixed solution remains outside the hemolytic activity range of SO.

10. The method of claim 8 in which step (a) further comprises (1) preparing at least one dried sample of SO said SO having a pH in solution outside the hemolytic activity range of SO; and (2) mixing each sample of SO with a non-hemolyzed blood or serum sample in a nonhemolytic solution, whereby the pH of the mixed solution remains outside the hemolytic activity range of SO.

11. The method of claim 8 in which step (a) further comprises.

(1) diluting a non-hemolyzed blood or serum sample in a non-hemolytic solution;

(2) introducing equal volumes or graduated volumes of the blood or serum sample solution into each of a series of test chambers; and (3) adding and mixing into each of the test chambers containing the blood or serum samples equal concentrations or graduated concentrations of SO hemolytically inactivated by pH, whereby the pH of the mixed solution in each test chamber remains outside the hemolytic activity range of SO.

12. The method of claim 8 in which step (a) further comprises (1) introducing equal concentrations and graduated concentrations of a dried amount of SO hemolytically inactivated by pH into each of a series of test chambers;

(2) diluting a non hemolyzed blood or serum sample in a non-hemolytic solution; and (3) adding and mixing into each of the test chambers containing the SO equal volumes or graduated volumes of the non-hemolytic blood sample solution, whereby the pH of the mixed solution in each test chamber remains outside the hemolytic activity range of SO.

13. The method of claim 8 wherein (a) the mixing of the blood or serum sample with the SO is conducted at a pH of at least about 9.4;

(b) each mixed solution comprising the blood or serum sample and the SO is incubated at a temperature in the range between room temperature and about 50° C.; and (c) each incubated solution is adjusted to a pH within the range of about 6 to about 8.

14. The method of claim 8 wherein (a) the mixing of the non-hemolyzed blood or serum sample with the SO is conducted at a pH of at least about 9.5–9.6;

(b) each mixed solution comprising the blood or serum sample and the SO is incubated at about 20°–25° C.; and (c) each incubated solution is adjusted to a pH within the range of about 6.5 to about 7.0.

15. A method for measuring the antistreptolysin (ASO) titer in a sample of blood or serum comprising the steps of (a) diluting a non-hemolyzed blood or serum sample with a non-hemolytic solution;

(b) introducing an equal volume of the diluted blood or serum into a plurality of test chambers, each of said test chambers containing different known amounts of a dry reversibly hemolytically inactivated SO wherein SO has been inactivated by contacting in a basic or buffered solution of a pH greater than about 9.4;

(c) mixing each sample of diluted blood with the SO;

(d) incubating each mixed solution comprising the blood or serum sample and the SO at a temperature ranging from about room temperature (18°–21° C.) to about 50° C. for about 1 to 10 minutes;

(e) restoring the hemolytic activity of the SO by adjusting the pH of each incubated solution to a pH ranging from about 6 to about 8; and (f) determining the ASO titer by detecting the presence or absence of lysis in each incubated solution about 5 to about 25 minutes after adjusting the pH of each said solution.

whereby a clear solution indicates the presence of lysis and an ASO titer of the sample less than that needed to bind the known quantity of SO, and a turbid solution indicates the absence of lysis and an ASO titer in the sample equal or greater than that needed to bind the known quantity of SO.

16. A method for measuring the antistreptolysin (ASO) titer in a sample of blood or serum comprising the steps of (a) serially diluting a non-hemolyzed blood or serum sample with a non-hemolytic solution;

(b) introducing equal volumes of the serially diluted blood or serum sample into a plurality of test chambers, each of said test chambers containing an equal amount of a dried reversibly hemolytically inactivated SO wherein said SO has been inactivated by contacting in a basic or buffered solution at a pH of at least about 9.4;

(c) mixing each sample of the serially diluted blood with the SO;

(d) incubating each mixed solution comprising the blood or serum sample and the SO at a temperature ranging from about room temperature (18°–21° C.) to about 50° C. for about 1 to 10 minutes;

(e) adjusting the pH of each incubated solution to a pH ranging from about 6 to about 8; and (f) determining the ASO titer by detecting the presence or absence of lysis in each incubated solution about 2 to about 20 minutes after adjusting the pH of each said solution, whereby a clear solution indicates the presence of lysis and an ASO titer of the sample less than that needed to bind the known quantity of SO, and a turbid solution indicates the absence of lysis and an ASO titer in the sample equal or greater than that needed to bind the known quantity of SO.

17. A method for monitoring the course of a disease state or infection arising from a group A streptococcus infection comprising (1) measuring the antistreptolysin O (ASO) titer in blood samples taken from the same subject at different times during the course of said disease state or infection and said measuring comprising the steps of (a) mixing at least one sample of non-hemolyzed blood with a predetermined quantity of Streptolysin O (SO) in a non-hemolytic solution having a pH outside the hemolytic activity range of SO, said SO having a known hemolytic capacity, and the pH of said solution being greater than about 9 or less than about 4.8;

(b) incubating each solution comprising the blood sample and the SO at a temperature of about 0°–50° C. for a time sufficient to allow any ASO in the sample to react with the SO;

(c) restoring the hemolytic activity of the SO by adjusting the pH of each incubated solution to a pH within a range of about 4.8 to about 9.0, whereby any free SO in excess of the amount required to react with the ASO can lyse blood; and (d) determining the ASO titer by detecting the presence or absence of lysis in each solution, whereby a clear solution indicates the presence of lysis and an ASO titer of the sample less than that needed to bind the known quantity of SO, and a turbid solution indicates the absence of lysis and an ASO titer in the sample equal or greater than that needed to bind the known quantity of SO; and (2) determining from successive measurements changes in the ASO titer from said subject;

whereby measured increases in the ASO titer indicates progression of said disease state or infection, and whereby measured decreases in the ASO titer indicates regression or cure of said disease state or infection.

* * * * *